United States Patent [19]
Planck et al.

[11] Patent Number: 5,145,250
[45] Date of Patent: Sep. 8, 1992

[54] PROCESS FOR THE PREPARATION OF BONE CEMENT

[75] Inventors: Heinrich Planck, Nürtingen; Christoph Elser, Plochingen; Albrecht Grieben, Darmstadt; Werner Ege, Frankfurt, all of Fed. Rep. of Germany

[73] Assignee: Merck Patent Gesellschaft mit beschraenkter Haftung, Darmstadt, Fed. Rep. of Germany

[21] Appl. No.: 538,816

[22] Filed: Jun. 15, 1990

[30] Foreign Application Priority Data

Jun. 15, 1989 [DE] Fed. Rep. of Germany ....... 3919534

[51] Int. Cl.$^5$ ............... B28C 7/04; B01F 13/06
[52] U.S. Cl. ........................... 366/8; 366/65; 366/139; 366/145; 366/149; 366/152; 366/177; 366/197; 366/249; 366/289; 422/225
[58] Field of Search ............... 366/2, 4, 6–8, 366/65, 131, 132, 134, 136, 137, 139, 144, 145, 147, 149, 151, 152, 160, 162, 177, 181, 197, 199, 241, 244, 247, 251, 255, 279, 330, 332, 333, 289; 422/109, 207, 224, 225, 227, 99; 99/348; 604/80, 82, 65, 86, 407, 411–415; 606/92–94

[56] References Cited

U.S. PATENT DOCUMENTS

| | | |
|---|---|---|
| 2,168,270 | 8/1939 | Paisley et al. ............... 604/415 X |
| 2,295,098 | 9/1942 | Cornell, Jr. ............... 366/149 X |
| 2,416,391 | 2/1947 | Hixson ............... 604/411 X |
| 3,085,000 | 4/1963 | Lupfer ............... 422/109 |
| 4,169,681 | 10/1979 | Kato ............... 366/255 X |
| 4,304,177 | 12/1981 | Loeffler et al. ............... 366/148 X |
| 4,758,096 | 7/1988 | Gunnarsson ............... 366/139 |
| 4,803,086 | 2/1989 | Hedenberg ............... 99/348 X |
| 4,854,716 | 8/1989 | Ziemann et al. ............... 366/139 |
| 4,889,432 | 12/1989 | Patterson ............... 366/139 |
| 4,973,168 | 11/1990 | Chan ............... 366/139 |

FOREIGN PATENT DOCUMENTS

| | | |
|---|---|---|
| 178658 | 4/1986 | European Pat. Off. ............ 366/139 |
| 971839 | 1/1951 | France ............... 604/414 |
| 234233 | 3/1986 | German Democratic Rep. ............... 366/144 |
| 147142 | 11/1980 | Japan ............... 366/139 |

*Primary Examiner*—Philip R. Coe
*Assistant Examiner*—C. Cooley
*Attorney, Agent, or Firm*—Millen, White & Zelano

[57] ABSTRACT

A process for the preparation of bone cement for subsequent introduction into the cavity of a bone serving to receive a prosthesis. The components serving for the production of the bone cement are introduced into a cartridge and mixed together during a mixing phase and subsequently undergo a further resting phase. The mixing phase and the resting phase are under automatic program control.

13 Claims, 4 Drawing Sheets

PROCESS FOR THE PREPARATION OF BONE CEMENT

BACKGROUND OF THE INVENTION

The invention relates to a process for the preparation of bone cement and to an apparatus for carrying out this process.

Bone cement serves to fix prostheses in the bones of human and animal bodies. A good and permanent bonding of the bone cement to a prosthesis and to the bone requires that the bone cement is satisfactorily prepared before introduction into the cavity of the bone concerned, which is to receive the prosthesis. This means, in particular, that the state of polymerization of the bone cement at the beginning of the introduction of the bone cement into the bone cavity is such that the processing of the bone cement which now takes place leads to the best possible, permanent anchoring of the prosthesis in the bone-cavity. The processing time, i.e., the time at the surgeon's disposal for carrying out all the required work to anchor the prosthesis in the correct position in the bone cavity, from the beginning of introduction of the bone cement into the bone cavity until the hardening phase of the bone cement begins and no longer permits any change in the position of the prosthesis, is to be fully sufficient.

Bone cement is in general produced by mixing of liquid methyl methacrylate monomer and pulverulent polymethyl methacrylate, possibly with the addition of hardeners and accelerators. However, bone cement can also be produced form any other suitable components.

SUMMARY OF THE INVENTION

An object of the invention is to achieve particularly good reproducibility of the state of polymerization of the bone cement at the end of the resting phase, this process being carried out with any polymerizable bone cements which can be produced from at least one pulverulent component and one liquid component, in each case in harmony with the bone cement concerned.

Upon further study of the specification and appended claims, further objects and advantages of this invention will become apparent to those skilled in the art.

In the process according to the invention, the course of the mixing phase and the succeeding resting phase during which the bone cement is produced from its components and prepared for its later introduction into a bone cavity is automatic with program-control and/or process-control. This makes it possible to achieve particularly good reproducibility of a state of polymerization desired at the end of the resting phase for the bone cement concerned, uninfluenced by human inadequacies. The state of the bone cement is thus placed at the disposal of the operating surgeon in a reproducible quality by the process according to the invention. This makes possible an optimization of the cement fixation of the prosthesis.

Program-controlled is to be understood as meaning that a program suited to the bone cement concerned is provided and can be stored on a program carrier and/or can be computed completely or partially for the respective bone cement and its amount, by a computer from data and/or measured values and the like to be input and/or stored, and controls at least one program step in the preparation of the bone cement during the mixing phase and/or the resting phase. The individual program step can be a fixed program step which can no longer be altered, or one which is dependent on at least one parameter, e.g., a program step which can be computed by a computer in dependence on the one or more parameter(s) concerned.

Process-controlled is to be understood as meaning that the preparation process of the bone cement during the mixing phase and/or the resting phase supplies, for its subsequent processing, at least one measured value derived from a sensor or transducer and/or at least one other signal, which is/are used to control this preparation process, which can also be called the production process, or, if program control is also provided, control it in addition to, and in conjunction with, the program control.

This will be explained in more detail with reference to a few examples.

When the room temperature in the operating theater concerned during the production of the bone cement has a known effect on the length of time of at least one program step, e.g., on the duration of the stirring of the bone cement components together and/or for the length of time of the resting phase, provision can be made to compute the length of time of the program step concerned in dependence on the room temperature forming a parameter, and to input the computed value into the program-control apparatus.

The program is thus varied in dependence on the room temperature. This is still not process control, only temperature-dependent program control. Thus if, e.g., the duration of the mixing phase and also the duration of the resting phase are established in dependence on the room temperature for the bone cement concerned, a computer computes the durations of these program steps, or a data field or a characteristic line field relating to this parameter can be stored and the program-control apparatus then seeks from the memory, or calculates using the relevant data stored in the memory, the valid program for this room temperature in dependence on the room temperature reported to it.

The quantity of bone cement to be produced, i.e., its volume or its weight, can also be a parameter, and the program will then be varied, in dependence on the respective quantity, which can be input into a computer by hand or by means of a data carrier which can be read by a reading device, likewise in dependence on this parameter or solely in dependence on this parameter.

In the same manner, provision can be made for the necessary data for many different bone cements to be input into the computer or a store associated with it, for process control and/or for program control, or for setting up the respective program, and the respective bone cement type is then input into the computer, which then computes the related program step(s), and/or process step(s) taking into account the existing parameter(s) and/or measured value(s), for this bone cement.

When process control is provided, a computer or a signal processing apparatus is supplied during the preparation of the bone cement with data on this preparation process, for example, the intrinsic temperature, sensed by a temperature sensor, of the mixture of components of the bone cement contained in the cartridge. The duration of the mixing phase and/or the duration of the resting phase is/are then adjusted or varied in each case according to this sensed temperature, or in dependence on this temperature, for example they are made shorter, the higher this temperature that occurs during the preparation process. Or the degree of polymerization of the bone cement during the resting phase is determined, and the resting phase is ended when a predetermined degree of polymerization is reached.

The invention makes it possible to prepare any bone cement automatically and reproducibly, so that at the end of the resting phase it has reproducibly reached the state of polymerization desired by the operating surgeon, who can thus introduce the bone cement into the bone cavity in the optimum state and fix the prosthesis in it.

It can also be provided, for process control, to sense the temperature above the mixture in the cartridge, or an intrinsic temperature of the cartridge, instead of sensing the temperature of the mixture in the cartridge.

It can be arranged, particularly advantageously, for the internal space of the cartridge to be shut off from the surrounding atmosphere, at least during the mixing phase, and connected at least intermittently, and preferably constantly, to a source of reduced pressure. This serves to ensure that the bone cement contains, at the end of the mixing phase or at the end of the resting phase, as few air inclusions as possible, thus improving its strength and durability in the bone cavity. It is already known per se to provide a reduced pressure in the cartridge during the mixing phase (EP-A2-0 178 658), and this is quite particularly advantageous in connection with the process according to the invention, since as a result the reproducibility of the state of the bone cement at the end of the resting phase is also still further improved. Standardization of the state of the bone cement, and thus also of the cementing procedure, is thus made possible.

It is further particularly convenient for the carrying out of the mixing phase, and likewise for the reproducibility of the preparation of the bone cement, if the stirrer element which performs stirring for mixing is completely immersed, during the mixing of the bone components, in the mixture of bone cement components present in the cartridge and/or is constantly or intermittently displaced in position, preferably moved up and down in the mixture, during the mixing process. It can also be particularly advantageous for the same purpose for the element which performs stirring to be a vane wheel like a propeller.

The preparation of the bone cement can be still further improved, particularly as regards the reproducibility of the state of polymerization of the bone cement at the end of the resting phase, in that the bone cement components are cooled at the beginning of the mixing phase to predetermined low temperatures. Cooling to temperatures of 0° to 10° C., preferably 4° to 8° C. is particularly recommended for the so-called "Standard Viscosity" bone cements, which can be mixed only with difficulty in vacuum at room temperature.

As a result of these low temperatures of the bone cement components at the beginning of the mixing phase, the polymerization of the bone cement takes place more slowly, and the mixing phase and the resting phase can therefore be lengthened, and even better reproducibility of the bone cement at the end of the resting phase can thus be attained.

In many cases it can also be appropriately arranged that the cartridge is at least intermittently heated and/or cooled during the mixing phase and/or during the resting phase, such that the rate of polymerization of the bone cement is thereby affected in a predetermined manner, e.g., slowed, and/or the bone cement at the end of the resting phase has a predetermined processing temperature, which is preferably lower than the room temperature of the operating theater concerned. The operating surgeon then knows exactly how much processing time is at his disposal for cementing the prosthesis into the bone cavity concerned, and the possibility of cementing defects is thus excluded or reduced. When, as is preferred, the temperature of the bone cement at the end of the resting phase is below the room temperature of the operating theater concerned, preferably considerably below, for example 5 to 20 Kelvin, sources of defects are then reduced and more precise implanting is made possible.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DISCUSSION

Figure 1:
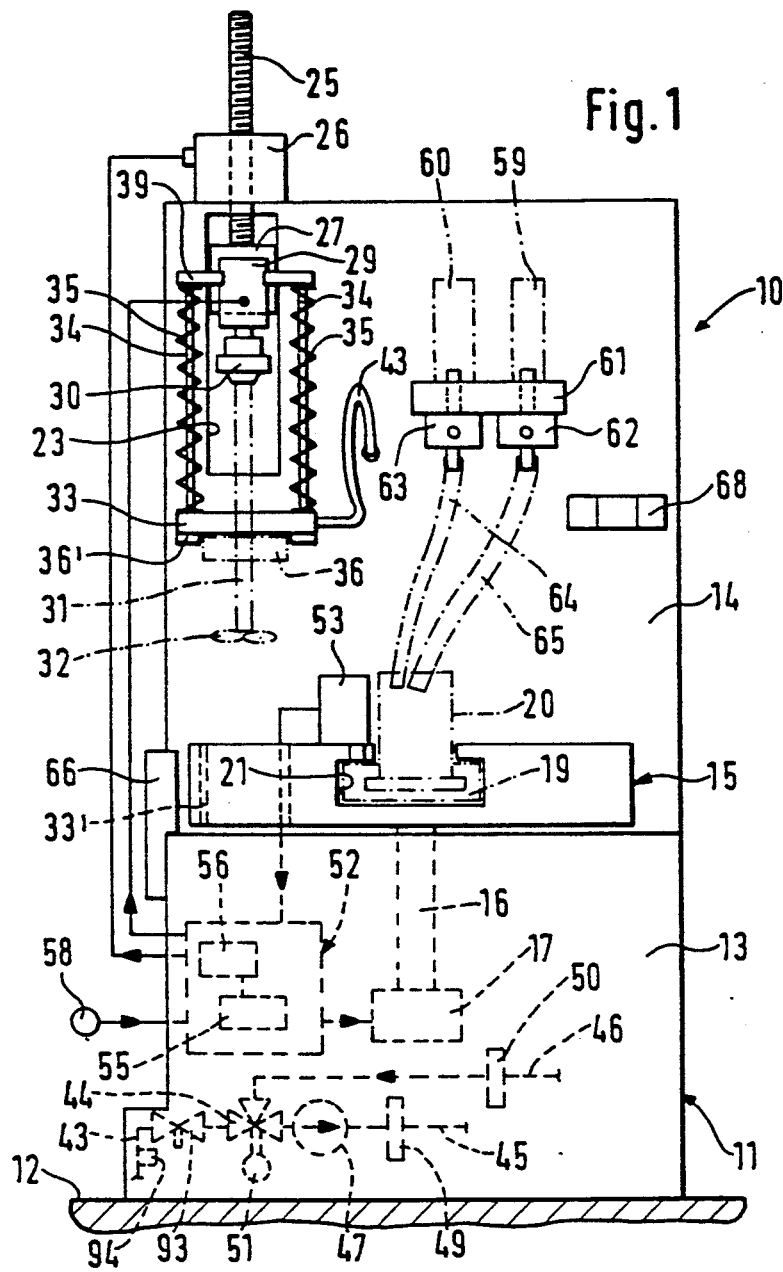
FIG. 1 shows a front view of a machine for preparing bone cement; a cartridge, a slide carrying it, and a stirring element with associated shaft, which are preferably all disposable articles, are indicated by dashed lines.

The machine 10 shown in FIGS. 1–4, which can also be termed equipment or apparatus, serves for the preparation of bone cement for subsequent introduction into a cavity of a bone, of a human or possibly of an animal, which is to receive a prosthesis. It has a frame 11 on which all of its components are arranged. It will be briefly referred to below as the "machine". It is of course also possible to arrange one or other of its components, e.g., its program-control apparatus and/or process-control apparatus, not on the frame 11 but, e.g., on a control desk separate from the frame 11 and connected to it by electrical and, if necessary, other flexible or non-flexible ducts.

The frame 11 has a box 13 placed on the floor 12 of an operating theater, on the upper side of which box a vertical stand 14 is firmly arranged on the rearward end of the box 13.

Figure 3:
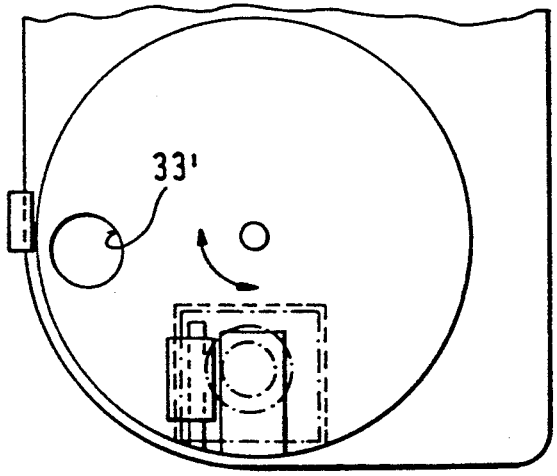
FIG. 3 shows a plan view of the rotary table of the machine according to FIGS. 1 and 2.

A rotary table 15 is arranged on the upper side of the box 13, and is capable of limited rotation about a vertical axis; its shaft 16 is rotatably mounted, in a manner not shown in greater detail, in the box 13 and is adjustable in angle between two positions by means of a drive motor 17. The one position, which is shown in FIGS. 1 and 3, is termed the basic position and serves for the introduction and removal again of a slide 19 in a straight guide 21 which is radial with respect to the axis of rotation of the rotary table and is arranged in the rotary table 15.

A cartridge 20 is inserted into, and held in, this slide 19, before or after (taking sterility into account) the slide is inserted into the straight guide 21. For this purpose, the cartridge 20, which can consist, for example, of opaque plastic, has a bottom annular flange 22 (FIG. 4) by which it is pushed, as far as an end position bounded by a stop, into a straight guide 95, which forms a receiver for the cartridge 20, in the slide 19, as can most clearly be seen in FIG. 4. The cartridge 20, which has an axially movable floor 18 acting as a piston and serving for the later pressing out of the prepared bone cement, projects upwards with its preferably cylindrical peripheral wall through an aperture of the slide 19 and a slot of the rotary table 15, above the rotary table 15.

A vertical straight guide 23 is arranged on the stand 14, and a slide 24 is mounted in it, e.g. guided in a straight line by means of a dovetail guide. At the top of the slide is fixed a threaded spindle 25, which can be moved vertically up and down by means of a drive motor 26 fixed to the stand 14. For this purpose, a threaded nut (not shown) is rotatably mounted in the drive motor 26 and can be driven in both directions of rotation by the motor of this drive motor 26. The threaded spindle 25 penetrates through this threaded nut, with a positive connection.

A horizontal boom or arm 27 is fixed on the slide 24, and a drive motor 29 with a vertical axis of rotation is fixed to its front end. A clamping device 30 is fixed to the output shaft of this drive motor 29 and serves to clamp a shaft 31 of a stirrer element 32 constructed as a propeller. This clamping device, which has, e.g., a collet chuck, can be opened and closed by a manually actuated operating member, here a ring.

A vertical passage hole 33' is arranged in the rotary table 15, and in the basic position of the rotary table 15 as shown in FIGS. 1 and 3 is aligned with the axis of rotation of the clamping device 30 and makes it possible to insert the shaft 31 together with the propeller 32 fixed to it through an opening of a pressure plate 33 into the clamping device 30, and to remove it again, so that this shaft 31 with the stirrer element 32 can easily be interchanged manually. As explained in further detail below, this shaft 31 with the stirrer element 32 can preferably be a sterile packed disposable article which is used only once in the production of a bone cement and is then discarded as waste. When the shaft 31 with the propeller 32 is inserted, the pressure plate 33, which is carried by the slide 24 in a manner described in more detail below, and which can also be termed as "pressure part", is in its uppermost position, or in any case in a raised position such that the shaft 31 with the propeller 32, when inserted into the hole 33' of the rotary table, can be introduced from below through the hole in the pressure plate 33 and then pushed further up until it is in the clamping device 30. The clamping device is then closed and thus holds the shaft 31 firmly, with a positive and frictional connection. Removal of the shaft 31 with the propeller 32 takes place, vice versa, after releasing the clamping device 30.

The function of the pressure plate 33 is further explained below. It is guided vertically in a straight line on two vertical guide rods 34 on which compression springs 35 are arranged which constantly load it. The compression springs 35 press it onto stops, such as 36', attached to the guide rods 34 at the lower side, and this pressure plate 33 is lifted from these stops when it presses a cover 36, which comes into abutment with its lower side and which in turn has an elastic seal 37 arranged on its lower side, onto the upper edge of the respective cartridge 20.

The two guide rods 34 are attached at the top to horizontal arms 39 which are fixed to the housing of the drive motor 29 and on which the compression springs 35 are supported at the top.

The cover 36, which is preferably likewise a sterile packed disposable article, since it serves only to close the cartridge 20 during the preparation of a single bone cement and therefore can be discarded as waste, together with the cartridge, after a single use, consists substantially of a plastic body which has a central passage hole through which the shaft 31 penetrates, the shaft 31 penetrating two O-rings 39' of the cover 36 which act to seal airtightly the hole through which the shaft 31 passes, without hindering the axial displaceability of the shaft 31 relative to the cover 36. This cover 36 is pushed onto the shaft 31 and held frictionally by the O-rings 39', before the shaft is clamped in the clamping device 30 as described above.

This cover 36 has a vertical air channel 40 and is rotated, on insertion of the shaft 31 into the clamping device 30, into an angular position relative to the pressure plate 33 such that this air channel 40, when this pressure plate 33 is pressed onto the cover 36, and thus when the pressure plate 33 abuts the upper side of the cover 36 to press the cover 36 onto the upper edge of the cartridge 20, communicates with an angled-down air channel 41 of the pressure plate 33. An annular seal 42 is placed into the cover 36 which seals off the air channels 40 and 41 from the exterior at their junction point.

A flexible air duct 43 is connected to the air channel 41 in the pressure plate 33, and leads to a 3-way valve 44, shown dashed in FIG. 1, fitted in the box 13 and connected by its two other connections to air ducts 45 and 46.

A suction pump 47 serving as a source of reduced pressure and an active charcoal filter 49 are interposed in the air duct 45, and a sterile filter 50 is interposed in the air duct 46. This 3-way valve 44 can be changed over by means of a servomotor 51.

The motor 17 rotating the rotary table 15 can preferably be a pneumatic or hydraulic working cylinder, but can have another kind of construction, e.g., it can be an electric motor.

A program-control and/or process-control apparatus 52 is arranged in the box 13 and serves for the program control and/or process control of the mixing phase and the resting phase in the production of the respective bone cement, and/or can serve for carrying out at least one process-controlled step in the preparation of the respective bone cement.

This apparatus 52 is for simplicity termed the "control apparatus" below.

A temperature sensor 58 is connected to this control apparatus 52 and senses the room temperature of the operating theater in which the machine 10 is set up.

The control apparatus 52 serves for automatic complete control of the preparation of the respective bone cement in a cartridge 20.

A reading device 53 is connected to the control apparatus 52, is arranged on the rotary table 15, and can read, through a slotted hole or slot 54 in the rotary table 15, markings or the like forming coded data arranged on the slide 19. The data concerned here give the type of the bone cement to be produced, i.e., prepared, and its amount, and the reading device 53 reads these data, preferably in a contactless manner, and signals them to a computer 55 of the control apparatus 52. A memory 56 is connected to this computer 55. Data are stored in this memory 56 in the form of a data field or a field of characteristic curves, as required by the computer 55 in order to compute from them the control steps for the mixing phase and the resting phase, which steps serve for the automatic control of the preparation of the respective bone cement, and then correspondingly to control these two phases automatically and for the bone cement concerned and its respective designated amount, in order thus to prepare the respective bone cement reproducibly and automatically.

For each type of bone cement to be prepared on this machine 10, data can then be stored in the memory 56 for the control steps to be computed for different room temperatures sensed by the room temperature sensor 58, as they are controlled in the operating theater according to the operation.

Data for bone cement types which were not originally provided can also be subsequently stored in this memory 56, and earlier data for bone cement types which are no longer used can be erased again.

Figure 5:
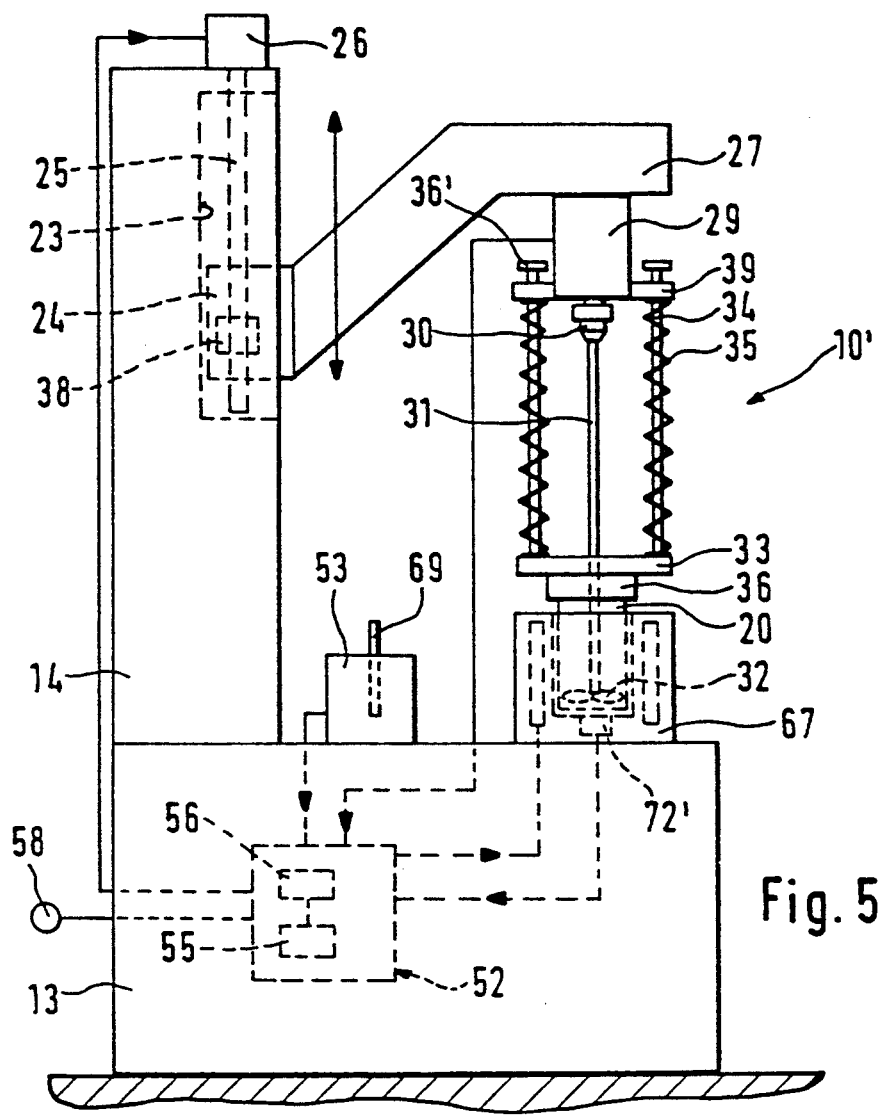
FIG. 5 shows a side view of a second exemplary embodiment of a machine for the preparation of bone cement.

For example, the data for a given bone cement type can be stored in the form of characteristic curves or data sequences, the parameter for the characteristic curves of this field of characteristic curves, or the data sequences of a data characteristic field, being the room temperature in the operating theater, as sensed by the room temperature sensor 58, or the temperature of the respective cartridge or the internal temperature of the cartridge 20, as sensed by a temperature sensor 72' (FIG. 5). The characteristic curve or data sequence concerned then indicates to the computer 55 the data for the bone cement concerned, dependent on the amount of the bone cement to be prepared, from which data the computer then computes the control steps for the mixing phase or the resting phase; and further process-dependent data, e.g. the temperature of the cartridge at any given time, can be signalled to the computer 55 even during control, for correction of the control steps which are in progress.

Such data sequences can be derived experimentally for each bone cement type. In the following example, a data sequence of a bone cement from the so-called "Standard Viscosity" bone cement group will explain this further.

| Room Temperature °C. | Temperature of components, °C. | Stirring time sec. | Resting phase until | |
|---|---|---|---|---|
| | | | min. | sec. |
| 17 | 4 | 30 | 4 | 30 |
| 20 | 4 | 30 | 4 | 00 |
| 23 | 4 | 30 | 3 | 30 |

-continued

| Room Temperature °C. | Temperature of components, °C. | Stirring time sec. | Resting phase until | |
|---|---|---|---|---|
| | | | min. | sec. |
| 17 | 8 | 25 | 4 | 00 |
| 20 | 8 | 25 | 3 | 30 |
| 23 | 8 | 25 | 3 | 00 |

It should further be stated here that with the so-called "low viscosity" bone cements, the components mostly should not be cooled, or should be cooled only for very high room temperatures, so that the resting phase does not become unnecessarily long.

A few modes of operation of this machine 10 are set forth as follows:

Exemplary of bone cement used to practice the invention is bone cement prepared analogously to known bone cements. These bone cements are prepared in such a way that approximately two parts of a finely particulate prepolymer containing a polymerization catalyst (for example dibenzoyl peroxide), in particular polymethyl methacrylate or a copolymer of methyl acrylate and methyl methacrylate, are mixed with approximately one part of the liquid monomer, for example methyl acrylate or methacrylate or mixtures thereof, containing an accelerator (for example dimethyl-p-toluidine), to give a formable composition which is implanted into the body and cures therein. Such bone cements are commercial available, for example under the trademark Palacos ®. In addition, pharmacologically active substances such as, for example, antibiotics or materials which facilitate anchorage of the bone cement in the body such as, for example, absorbable tricalciumphosphate can also be incorporated therein.

The operation of the machine in accordance with the instant invention will now be described.

The slide 19, acting as a data carrier, is provided with the data on the type of bone cement and the amount of the bone cement to be produced. The cartridge 20, empty to begin with, is inserted in the slide 19. The slide 19 with cartridge 20 is then pushed up to the stop, into its predetermined position in the straight guide 21 of the rotary table 15. The shaft 31 with the propeller 32 and the cover 36 pushed onto it is inserted in the clamping device 30. The components of the bone cement to be produced are located in two storage vessels 59, 60, which are set up on a holder apparatus 61 arranged on the stand 14. The storage vessel 59 contains liquid monomer, if necessary with additions of hardener or the like, and the storage vessel 60 contains the pulverulent components of the bone cement to be produced. If necessary, provision can also be made to charge the cartridge 20 manually in a conventional manner with the predetermined contents of a monomer ampoule and a polymer powder bag.

These storage vessels 59, 60 contain these components in excess in this exemplary embodiment, and a respective metering apparatus 62, 63, which can be manually adjusted, is therefore arranged on this holding apparatus 61 for the exact metering of the amounts of these components required for the amount of the bone cement to be produced. The storage vessels 59, 60 are connected to these metering apparatuses 62, 63 by short ducts, and ducts for removal of air (not shown) can also be connected in order to facilitate removal without difficulty of the concerned amounts of components from these storage vessels 59, 60.

A respective flexible duct 64, 65 is connected to the outlet of each of the two metering apparatuses 62, 63, and is introduced into the open cartridge 20, as shown by dash-dot lines in FIG. 1. Provision can now be made for the metering devices 62, 63 to be manually activated, or provision can also be made for them to be activated by the control apparatus 52. As a result of their activation, they remove from the storage containers the preset amounts of the two components, which are thus introduced into the cartridge 20 through the ducts 64, 65.

Figure 2:
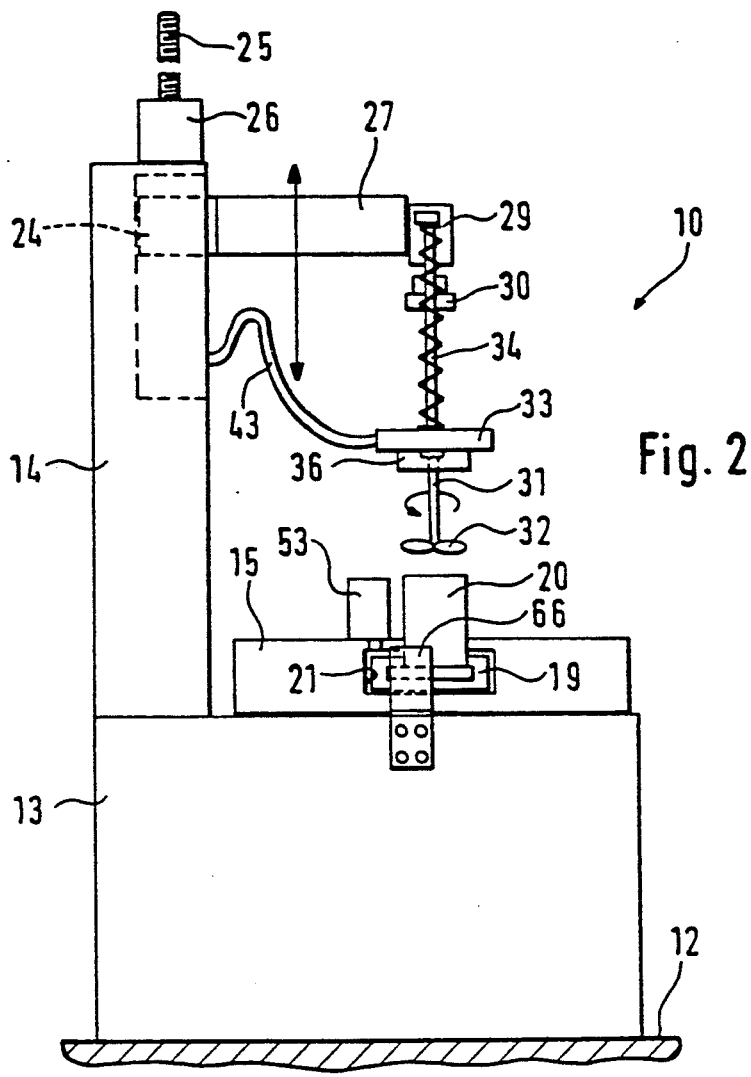
FIG. 2 shows a side view of the machine according to FIG. 1.
Figure 4:
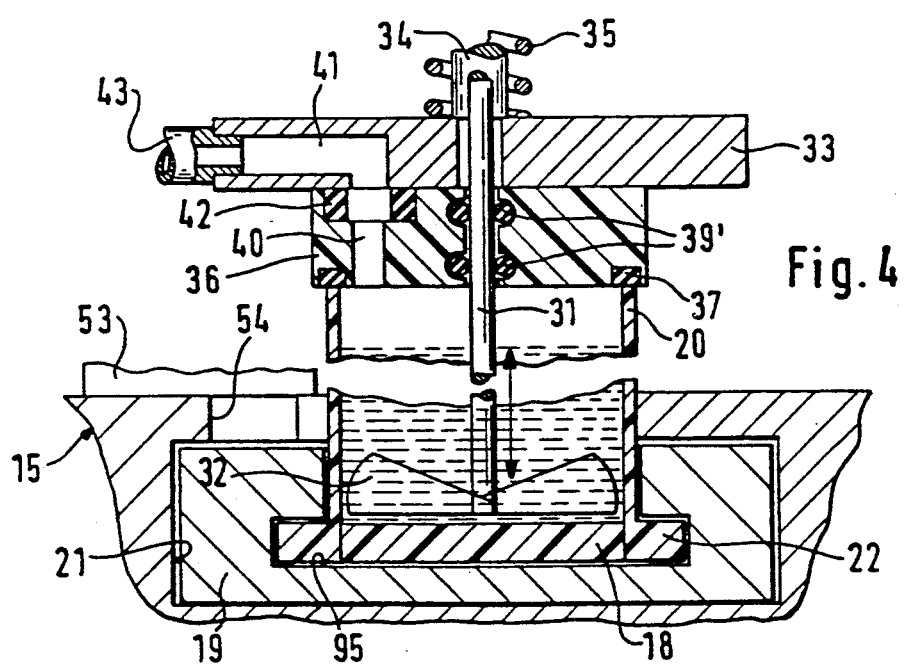
FIG. 4 is a broken-away representation of a longitudinal section through a cartridge, which is held on the rotary table of the machine according to FIG. 1, and onto which a cover is pressed by means of a plate-like pressure part of the machine according to FIGS. 1 and 2.

After the two components have been charged into the cartridge in the predetermined amounts, the ducts 64 and 65 can be withdrawn from it, or they pull themselves, at the start, which now takes place, of rotation of the rotary table 15 out of the position shown in FIG. 1 and corresponding to the basic position into its working position, which in this exemplary embodiment is angularly offset by about 90°, as shown in FIG. 2. Stirring of the components charged into the cartridge 20, and preferably also the succeeding resting phase, take place in this working position. Initiation of this rotary motion, which can be ended by a limit switch (not shown), can take place manually or by means of the control apparatus 52. In this working position, a metallic shield 66, for example, acting as a stop, is located exteriorly on the box 13, immediately opposite the straight guide 21 of the rotary table 15, and makes it impossible to take the slide 19 with the cartridge 20 out of the straight guide 21, thus ensuring that the cartridge 20 cannot be inadvertently removed from the rotary table 15 during the mixing of the components and possibly also during the resting phase.

As soon as the rotary table 15 has reached its designated working position, the arm 27 can be lowered, together with the parts which it carries, by means of the motor 26 until it reaches a predetermined position in which the propeller 32 is located within the cartridge 30 and the cover 36 is sealingly pressed on the top edge of the cartridge 20 and seals its interior airtightly from the surroundings. This is signalled, e.g. by a limit switch, to the control apparatus 52, and this then next activates, at the latest, the reading device 53 to read the indications contained on the slide 19 concerning the amount and type of the bone cement concerned. The reading device 53 signals these to the computer 55, which now, preferably in a dialog with the memory 56, computes the necessary data in the designated sequence for the control of the mixing of the components present in the cartridge 20 and for the subsequent resting phase, these data taking into account the value of the room temperature reported by the room temperature sensor 58, for the type and amount of the bone cement concerned.

Equally well, whether the control apparatus 52 already controls the travel of the propeller 32 into the cartridge, or whether the lowering of the arm 27 is initiated manually, provision can be made that, during the travel of the propeller 32 into the cartridge 20, the shaft 31 and hence the propeller 32 serving as stirrer element are already in rotation, or the arrival can be awaited of the propeller 32, which can also be termed a vane wheel, in a designated position within the cartridge 20 in which it can already, in appropriate circumstances, be dipped into the components present in the cartridge 20, or the taking over of control of the drive motor 29 by the control apparatus 52 can be awaited. When the propeller is already rotating when introduced into the cartridge or into the components present in it, this can preferably take place with an initial low speed of rotation. A higher speed of rotation of the propeller 32 can then be switched on at a programmed later instant, or this higher speed of rotation can be exclusively switched on. Even other possibilities exist, e.g., programmed or process-controlled constant or multiple stepwise adjustment of the speed of rotation of the propeller 32 during mixing.

The radius of rotation of the propeller 32 is only slightly smaller than the internal diameter of the cartridge 20, which is possible because the axis of rotation of the shaft 31 is aligned with the longitudinal axis of the cartridge in the working position of the rotary table 15. The propeller 32 is also approximately planar on its underside and can be lowered almost as far as the floor of the cartridge 20.

Mixing together of the components present in the cartridge 20 by the stirrer element 32 now takes place. This stirrer element 32 is continuously moved up and down for mixing during the mixing phase, in dependence on the amount of bone cement components present in the cartridge 20, i.e., the height to which the cartridge is filled, whether it is during a programmed time interval or during a predetermined number of up and down strokes, or process-controlled by means of the reversible drive motor 26, which is controlled correspondingly to this by the control apparatus 52. The stroke height is set such that the propeller 32 constantly remains immersed in the bone cement mixture in the cartridge 20, and the upward stroke is preferably programmed such that it goes to just below the filled height of this mixture in the cartridge 20, and the downward stroke appropriately goes respectively (for the sake of particularly uniform mixing) to just above the floor 18 of the cartridge 20. The computer 55 computes from the data stored in the memory 56 not only the stroke height of the propeller 32 for its stroke motions, but also, taking account of room temperature and the filling amount, the required period of time, or the number of strokes of the propeller 32 up to the end of the mixing phase, for the intimate mixing of the two components to give bone cement.

As soon as the cover 36 has been pressed by the pressure plate 33 onto the cartridge 20, the suction pump 47 which forms the source of reduced pressure is switched on and effects a predetermined reduced pressure of the cartridge during stirring or at least intermittently during stirring. This reduced pressure can be e.g. 300 to 700 mm Hg, preferably 400 to 600 mm Hg. Thus it is not necessary for the cartridge 20 to be completely empty of air, but a predetermined reduced pressure can be produced in it which is considerably lower than the atmospheric pressure in the operating theater. This suction pump 47 serves to make the bone cement as air-free as possible, and in particular to prevent air inclusions. The reduced pressure pump 47 or vacuum pump can also remain switched on at least from time to time during the succeeding resting phase, or can be switched off. The control apparatus 52 switches off the motor 26 at the end of this mixing phase, preferably in a predetermined stroke position of the propeller 32, detaining it there. Indeed, it can also be conveniently provided here for the propeller to be withdrawn from the bone cement before stopping and for bone cement adhering to it to be centrifuged off by a high speed of rotation while still within the cartridge 20, and only then stopped.

The resting phase now begins, during which the polymerization of the bone cement slowly progresses. The computer 55 computes from the data indicated to it the duration of this resting phase, or this is ended in dependence on the process, e.g. when the temperature increasing due to polymerization of the bone cement has reached a predetermined difference value from the room temperature. When the resting phase has ended, or even before this, the control apparatus controls the raising of the slide 24 upwards into its position as shown in FIG. 1, in which the cover 36 is taken off the cartridge 20 again and the propeller 32 is pulled up out of the cartridge 20. At the end of the resting phase, or when the propeller is first moved out of the cartridge 20 at the end of the resting phase, the control apparatus 52, after this movement, orders the rotary table 15 to translate out of the working position (FIG. 2) into the basic position according to FIG. 1, in that the motor 17 is correspondingly switched on. This rotary motion can be ended, e.g., by means of a limit switch. As soon as the rotary table 15 has again taken up its basic position as shown in FIG. 1, this can be signalled optically or acoustically, and an operator, e.g. a nurse, now takes the slide 19 with the cartridge 20 out of the straight slide 21. A screw cap having an extrusion channel is then screwed onto this cartridge 20 and the operating surgeon now undertakes the filling of the bone cement into the related bone cavity of the patient; this takes place by pushing the movable floor of this cartridge 20, which forms a piston, in a known manner.

A display 68 is also arranged on the machine 10, on which important or required data can be indicated to the operating personnel, e.g. the type of the bone cement and its filling amount. The progress of the mixing phase and resting phase can likewise be indicated. Provision can also be made for the processing time of the bone cement at the disposal of the operating surgeon to be signalled on this display 68 after the end of the resting phase, e.g. by a countdown of the duration, in order to indicate at any given time what length of time is at his disposal until ending the installation of the prosthesis in the correct position. For the bone cement type concerned and its amount, the hardening time can also be indicated, e.g. likewise by a countdown. These indications can also be effected and controlled by the control apparatus 52.

It should now be mentioned that the reduced pressure to be produced by the suction pump 47 in the cartridge 20 can also be controlled or regulated, e.g., in that this pump 47 has a controllable r.p.m. or its input is connected not only to the 3-way valve, but also can exhaust dead air, e.g. from the internal space of the box 13, via a control valve 93 (FIG. 1), controlled by a control or by a reduced pressure regulator which can be, e.g., a part of the control apparatus 52. In the case of regulation, the control valve 93 causes dead air to be taken in by the pump 47 to such a degree that a set constant reduced pressure is produced in the cartridge 20, in that it is adjusted by the reduced pressure regulator by means of a servomotor, in dependence on the difference that forms the control deviation between a set reference value of the reduced pressure and the reduced pressure sensed by a pressure sensor 94 in the duct 43, such that this control deviation is diminished. In the case of control of the reduced pressure, the control valve 93 is adjusted according to the respective desired reduced pressure.

The beginning of the mixing phase can be arranged differently. In the simplest case, the operator of the machine 10 carries out the introduction of the bone cement components into the cartridge, in that he switches on the metering apparatuses 62, 63 manually and actuates a switch, after completion of the charging of components into the cartridge 20, to initiate the rotation of the rotary table 15 from its basic position into the working position. The limit switch which signals that this working position of the rotary table 15 has been reached can then actuate the control apparatus 52 for the initiation of the further automatic course of the mixing phase which now begins, and the ensuing resting phase, the control apparatus first controlling lowering of the pressure plate 33 to press the cover 36 onto the cartridge, and correspondingly the introduction of the propeller 32 into the cartridge 20. Or provision can also be made for this process of lowering of this pressure plate 33 on pressing the cover 36 onto the cartridge 20 and introduction of the propeller 32 into it to still be initiated manually by an operator, and only when the pressure plate 33 has pressed the cover 36 onto the cartridge, for a limit switch or the operator to actuate the control apparatus 52 for the automatic performance, which only now begins, of the mixing phase and the resting phase.

It is particularly advantageous for the automatic course of the mixing phase to be begun as soon as the operator has set up the storage containers 59, 60 on the holding device 61 and has introduced the ducts 64, 65 into the cartridge 20 in the basic position of the rotary table 15. Provision can then be made that either the operator, previously or now for the first time, sets the metering apparatuses 62, 63 manually to the amounts of the two components to be measured, or that this is automatically undertaken by the control apparatus 52 after the type of bone cement and the filling amount have been signalled to it by the reading device 53, in which latter case the ducts 64, 65 are not introduced into the cartridge 20 in the basic position of the rotary table 15, but before the introduction of these ducts 64, 65, the rotation of the rotary table 15 into its working position (FIG. 2) has already been ordered manually or by the control apparatus, and only then are the ducts 64, 65 introduced. In this case the control apparatus 52 can then control the required settings of the metering devices 62, 63 and their working, and it can also subsequently control, by means of a suitable mechanism, the lowering of the pressure plate together with the cover 36 and the propeller 32 onto or into the cartridge 20.

The beginning of the mixing phase can thus be arranged differently. In the extreme case, the automatic control of the mixing phase by the control apparatus 52 already begins before the charging of the components present in the supply containers 59, 60 into the cartridge 20, all of the required steps for the preparation of the bone cement being thereafter controlled by the control apparatus 52, such as setting the metering apparatuses 62, 63, and likewise also introducing the ducts 64, 65 into the cartridge 20, charging the components into the cartridge 20, lowering the pressure plate 33 with the cover 36 and propeller 32 until on or in the cartridge 20, subsequent stirring together of the components which are located in the cartridge 20, and subsequent control of the resting time.

In the other extreme case the mixing phase, which is automatically controlled, together with the subsequent resting phase, by the control apparatus 52, begins only when, effected by the operator, the two components have already been charged into the cartridge 20, the rotary table 15 has been rotated into its working position, and the respective cartridge 20 has already been closed by the cover 36 and the propeller 32 has already been introduced into the components present in the cartridge or in any case into the cartridge 20.

The beginning of the automatic control of the mixing phase can also be provided between these two extremes, e.g., on reaching the working position of the rotary table 15 or with the end of the charging of the components into the cartridge 20. Other modes of beginning the automatic control of the mixing phase by the control apparatus 52 can also be provided, between the two said extremes.

Thus in the sense of the invention the mixing phase begins at the moment from which the control apparatus 52 becomes active.

According to the above description of a few possible modes of operation of the control apparatus 52, this can operate as a pure program-control apparatus. Or process control can also, however, additionally take place, as explained below. For example, the temperature of the cartridge 20 during the mixing phase and possibly also during the resting phase can be sensed by a temperature sensor, and from the sensed temperature rise which occurs during the progress of the polymerization, conclusions are drawn as to the state of polymerization of the bone cement, and in particular as to its viscosity, and at least one control step is controlled in dependence on this state of polymerization. For example, the mixing phase and/or the resting phase can be ended in dependence on this state of polymerization and thus process-dependently.

Instead of the rotary table 15, a linearly or otherwise movable table can also be provided, which is displaceable in position between a basic position in which the cartridge 20 with slide 19 is pushed into a corresponding straight guide 21 and a working position in which the removal of the slide 19 with cartridge 20 from this straight guide is blocked.

It is also possible to arrange the straight guide 21 for the slide 19 on the box 13, among other things, immovably on or in its upper side, and to block the removal of the slide 19 with the cartridge 20 during operation of the stirrer element 32 and possibly also during the resting phase in another manner, e.g., by means of an automatically movable bolt, or provision can also be made to dispense with such a stop and to leave it to the precision of the operator that no inadvertent premature removal of the cartridge 20 from the machine takes place. Or this premature removal is blocked in that the pressure plate 33 presses the cover 36 onto the cartridge up to the end of the resting phase. The resting phase is in this case ended as soon as the pressure plate 33 is taken away from the cartridge, together with the cover 36 and the propeller 32.

In some cases it can also be provided that the resting phase, or a part of the resting phase, takes place with the cover 36 already removed, as long as the monomer vapours possibly escaping from the cartridge do not cause trouble or are sucked away.

In the machine 10' shown in FIG. 5, parts which correspond or can correspond to parts of the machine 10 according to FIGS. 1 to 4 or which have the same purposes are referenced with the same reference numerals and therefore require no further explanation.

This machine 10' according to FIG. 5, likewise representing as apparatus for the preparation of bone cement to be introduced subsequently into a bone cavity which is to receive a prosthesis, differs from that of FIGS. 1 to 4 essentially in that the respective cartridge 20 is immovably arranged on the box 13 of the frame 11. It is here inserted, with a positive connection, into and extending somewhat over a recess of a tempering apparatus 67, and the propeller 32 is shown having already moved into it.

The reading device 53 is not used here to read data applied to a slide carrying the respective cartridge 20, but these data are located on a separate data carrier 69, e.g. constituted as a card.

The tempering apparatus 67 is used to cool and heat the cartridge 20 so that the bone cement located in it at any given time is affected, as regards its rate of polymerization, in a predetermined manner, which makes possible particularly precise control of the resting phase or particularly good control of the mixing. This tempering apparatus 67 also enables the processing time at the disposal of the operating surgeon after the end of the resting phase to be influenced, if the bone cement at the end of the resting phase has a predetermined temperature which has been raised or lowered by means of the tempering apparatus 67.

The machine 10' is shown in FIG. 5 in a working state, in which machine the propeller 32 is already located in the cartridge 20 concerned. It had been previously moved, as in the machine according to FIGS. 1 to 4, into the cartridge 20 from a position at a distance above the cartridge, the cover 36 having been moved with it by a downward motion of the pressure plate 33, which is likewise resiliently supported, after the components of the bone cement concerned had been charged into the cartridge 20 beforehand.

In this exemplary embodiment, the guide rods 34 are fixed on the pressure plate 33, and are guided linearly by arms 39 attached to the drive motor 29, in fact through guide holes of these arms 39; at the top they have stops 36' at their upper ends, which stops limit the downward motion of the pressure plate 33 relative to the boom 27.

The threaded spindle 25 is here firmly connected to the output shaft of the drive motor 26 and engages with a threaded nut 38 through which it passes and which is fixed to the slide 24.

Figure 6:
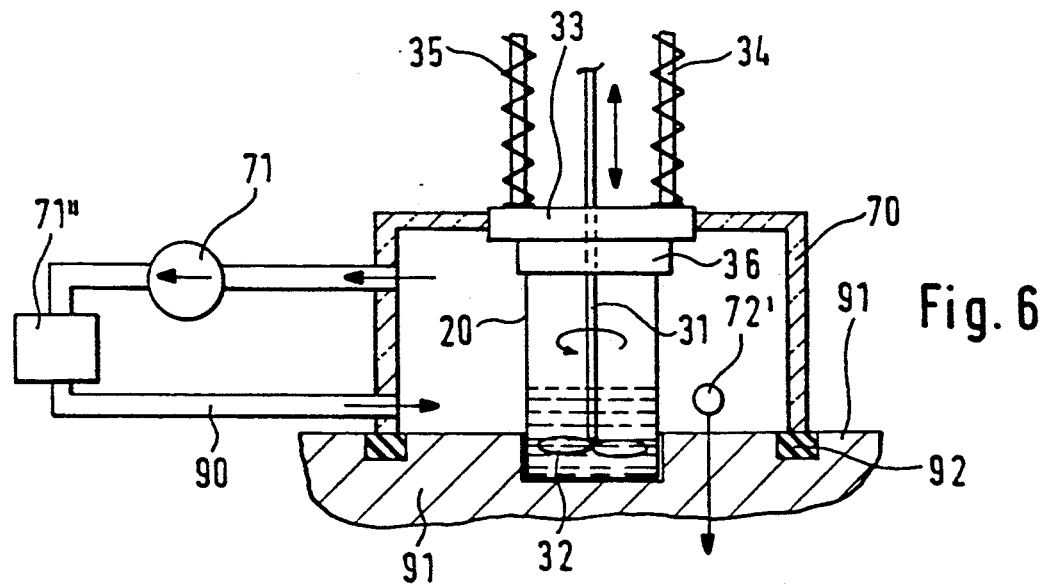
FIG. 6 shows a modification of a detail of the machine according to FIG. 5, in a partially sectional representation.

A modification of the tempering apparatus 67 of FIG. 5 is shown in FIG. 6. It has a hood 70 attached to the pressure plate 33 and located in its normal position far above the cartridge 20 respectively located in a recess of the immovable table 91 of the box 13. When a cartridge is set on the table 91 and the respective components of the bone cement to be produced are introduced into it, and the shaft 31 with the vane wheel 32 is clamped in the clamping device 30, the hood 70 is then moved downwards together with the pressure plate 33 by lowering the arm 27 far enough to be seated on a ring seal 92 let into the table 91. In this position of the hood 70, the resiliently supported pressure plate 33 presses the cover 36 located on the shaft 31 onto the upper edge of the cartridge 20 concerned. This hood 70 thus forms a space which is sealed from the exterior and within which the cartridge 20 is located during the mixing of the bone cement components previously charged into it, and preferably also during the resting phase of the bone cement. The interior of the hood 70 is connected to an external pump 71 which is interposed in an air circulation duct 90 leading back into the hood 70.

The air sucked out by this pump 71 is passed through a heating apparatus and/or cooling apparatus 71', likewise interposed in the air circulation duct 90 and is passed back into the interior of the hood 70 as heated or cooled circulating air, so that the respective cartridge 20 and thus the bone cement mixture contained in it are tempered in a predetermined manner which can be controlled by the control apparatus 52 and preferably also regulated by a regulator. In order to regulate this temperature, a temperature sensor 72' can be arranged within the hood 70, and is the actual value sensor of the actual value of the internal temperature of the hood 70 to be regulated by a regulator (not shown), and hence of the temperature of the cartridge 20 and of the bone cement or its components located in it. This regulator can be a part of the control apparatus 52 and its adjustable reference value can be computed by the computer 55 or be input in another manner, e.g. even manually, as may often be convenient.

In the machine according to FIG. 6 a temperature sensor 72' is also arranged in the interior of the tempering apparatus 67, senses the temperature of the cartridge 20 and hence the temperature of the bone cement mixture present in it at any given time, and signals it to a regulator (not shown) for the regulation of this internal temperature.

The components of the respective bone cement are introduced in an absolutely sterile state into the respective cartridge 20 when this has already been closed by the cover 36, loaded by the pressure plate 33. An exemplary embodiment by means of which this can be achieved is shown in FIG. 7.

The two components of the bone cement to be produced are here present in two ampoules 59' and 60', which have been charged in a sterile manner with the liquid monomer or the pulverulent components of the bone cement to be produced. These ampoules are each closed by septum 73, 74 forming an elastomeric diaphragm.

These ampoules or containers 59', 60' can contain these components in the amounts required for the production of the bone cement concerned, already precisely measured out, or it is also possible for them to have the components in excess and to measure them out by means of at least one metering device, which likewise must operate in a sterile manner. In this exemplary embodiment it is assumed, however, that these components are present in these ampoules 59', 60' in the designated amounts.

Figure 7:
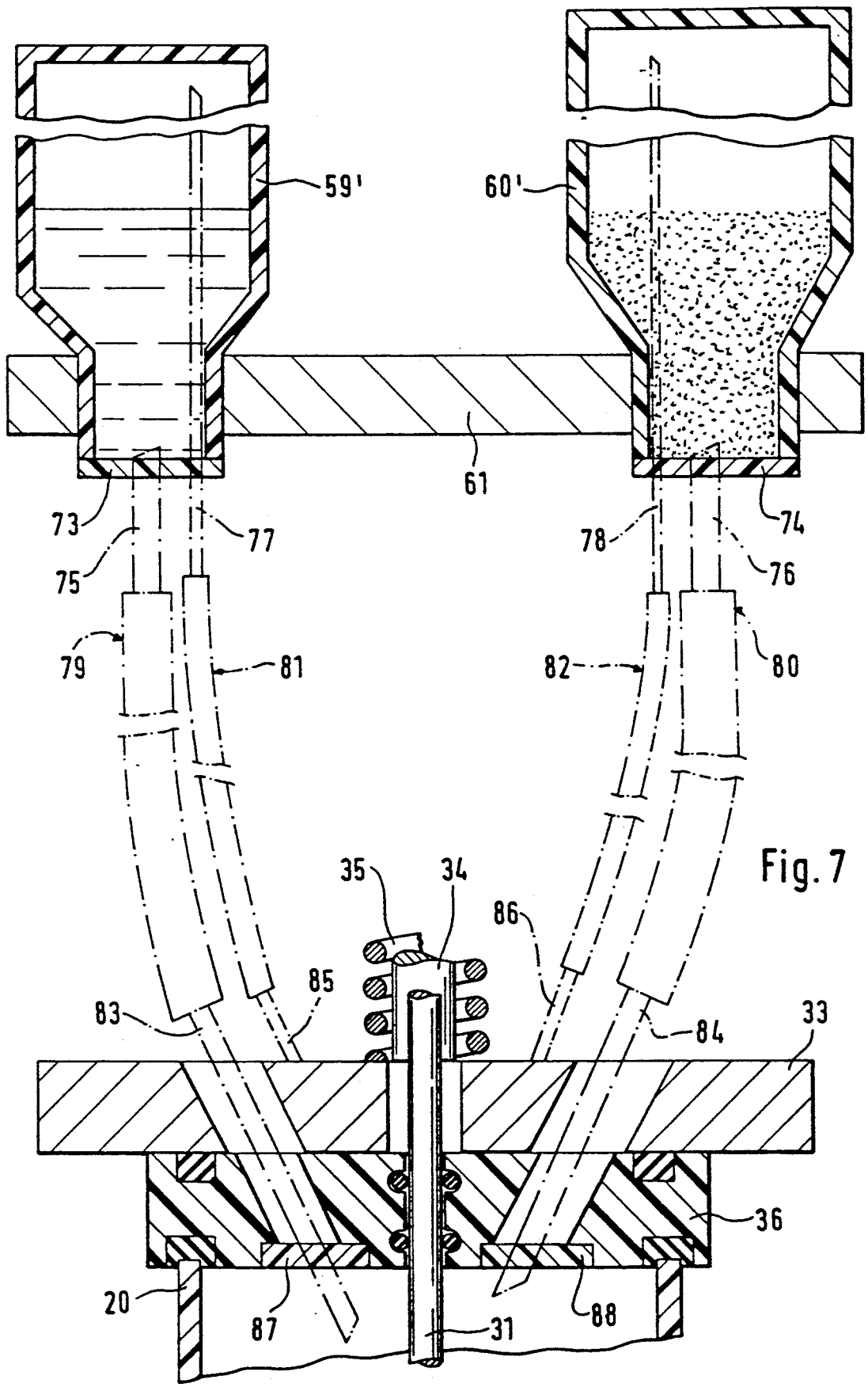
FIG. 7 shows, in a sectional representation, two ampoules which contain the liquid and pulverulent components of a bone cement to be produced; it is shown in dot-dash lines how this liquid, forming or containing a monomer, and the powder can be filled in a satisfactorily septic manner into the cartridge in which this bone cement is to be produced, e.g., on the machine according to FIG. 5.

The cover 36, which closes the associated cartridge 20 during the mixing phase and preferably also during the resting phase of the bone cement to be prepared in it, has a total of four holes, two of which can be seen in FIG. 7. Each such hole is blocked airtightly by a septum, such as 87, 88.

Sterilized flexible ducts 79 to 82 are used for the sterile removal of the two components from the ampoules 59', 60' and their transfer into the cartridge 20; a respecive cannula 75 to 78 and 83 to 86 is arranged at each of their two ends. The operator concerned pushes two cannulas 75, 77 or 76, 78 through each septum 73 and 74, the shorter cannulas 75, 76 being used for the removal of the components concerned and the longer ones for the deaeration of the interior of the ampoule 59' or 60' concerned.

Each of these cannulas 83 to 86 is pushed through a septum of the cover 36 until in the cartridge 20, these cannulas 83 to 86 penetrating the holes provided for them in the pressure plate 33 and the cover 36. The cannulas 83 to 86 are first pushed through the septa concerned, such as 87, 88, of the cover 36, and then the upper cannulas 75 and 76, and after them the deaeration cannulas 77 and 78 are pushed through the related septa 73, 74 of the ampoules 59', 60' and the components concerned now flow in a sterile manner through the ducts 79 and 80 into the cartridge 20. When this process is completed, the operator pulls the cannulas 83 to 86 out of the septa of the cover 36, of which only the septa 87 and 88 can be seen, these septa closing airtightly again, and then removes these ducts 79 to 82 and also the ampoules 59', 60' from the holding device 61.

Immediately after introduction of the two components into the cartridge 20 and removal of the cannulas 83 to 86, the mixing of the two components, filled into the cartridge in a sterile manner, can be commenced, for which purpose the propeller (not shown) effecting the mixing of these components is driven by means of the shaft 31. The propeller 32 can also already be set in rotation during the charging of the two components, or can be set in rotation only after this filling.

It is possible, without anything further, to provide for this sterile charging of the components into the respective cartridge 20 by any devices according to the invention, e.g., the machines 10 and 10'.

The control apparatus 52 can in some cases also act as a purely process-controlled apparatus, in that it is constructed thus and receives signals, from at least one sensor responding to the state of the mixture present in the respective cartridge 20 and being made into bone cement, i.e., the bone cement mixture, which state is to be process-controlled. This state, or such a state, can be the progress of the stirring or polymerization of the bone cement mixture. For example, the state of the bone cement mixture can be its toughness or viscosity and can be determined by a torque measuring device, this torque measuring device sensing the torque transmitted by the shaft 31 to drive the propeller 32. For example, this torque can be sensed by the instantaneous power consumption of the motor 29 divided by its speed of rotation, or can be sensed by a device which measures it directly. This torque is dependent on the progress of the mixing process of the bone cement mixture present in the cartridge 20.

All components useful in the process and apparatus of this invention, including all electronic and data processing aspects are per se conventional as in their interfacing, including microprocessors, memory units, interface devices (e.g., for input-output). Typically, all electronic and data processing functions of this invention are achievable using commercially available computers and interface devices. The latter can be routinely programmed to accommodate and utilize any data, parameter or other information mentioned herein to calculate other parameters (e.g., times) used to control the processes and apparatus of this invention, e.g., using known characteristics and properties of the bone cement components and their admixtures and the curing characteristics involved, or using routine preliminary experiments to determine such characteristics and properties.

The entire disclosures of all applications, patents and publications, if any, cited above and below, and of corresponding application(s) Federal Republic of Germany P 39 19 534, filed Jun. 15, 1989, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of bone cement for subsequent introduction into a cavity of a bone of a patient prepared to receive a prosthesis, wherein the bone cement is prepared in an apparatus including a sterile cartridge, stirrer and automatic controller, from components including at least one fluid material and a pulverized material, the process comprising the steps of:
   incorporating, with a data carrier associated with the cartridge, data specifying the type and amount of bone cement to be produced;
   reading the data into the automatic controller by inserting the sterile cartridge and associated data carrier into a holding apparatus of a receiver in the apparatus provided for receiving the sterile cartridge and being connected to the automatic controller;
   charging the sterile cartridge with the components in the amount and type specified by the data incorporated in the data carrier;
   under automatic control, beginning polymerization of the components into bone cement by stirring the components in the sterile cartridge with a stirrer during a mixing phase;
   under automatic control, allowing the mixed components to rest in a resting phase for a selected duration of time to achieve a selected state of polymerization; and
   reducing the pressure in the cartridge while the components are in at least one of the phrases to produce bone cement available for introduction into the cavity.

2. The process according to claim 1, wherein during the mixing phase and the resting phase the cartridge is isolated during selected times from the surrounding atmosphere and gas is then exhausted from the cartridge at least intermittently, by reducing the pressure within the cartridge, the exhausted gas being preferably passed through an active charcoal filter which filters out monomers contained therein, and wherein, when the reduced pressure existing in the cartridge due to exhausting of gas in the cartridge is released, the ambient air flowing into the cartridge is filtered through a sterile filter to filter out bacteria, viruses and the like which may be contained therein.

3. The process according to claim 1, wherein the mixing phase is initiated in conjunction with charging the cartridge with the components of the bone cement and the introduction of the stirrer, which stirrer serves to stir the components of the bone cement while in the cartridge.

4. The process of claim 1, wherein stirring is accomplished with a propeller completely immersed in the components, which propeller is displaced in axial position as it rotates by being axially reciprocated during the mixing phase.

5. The process according to claim 1, wherein the bone cement components are cooled at the beginning of the mixing phase to a predetermined low temperature.

6. The process according to claim 1, wherein the at least one pulverized component and the at least one fluid component of the bone cement to be produced are stored in storage vessels, and the components are dispensed into the cartridge, by means of a duct connected to the vessel through an adjustable metering device and wherein the stirrer is introduced into the cartridge only after the fluid component has been dispensed into the cartridge.

7. The process of claim 1, further comprising the steps of performing the steps in an operating theater having a selected room temperature and introducing the bone cement into the cavity at a selected time after its preparation.

8. The process of claim 7, wherein the selected time is determined by the duration of the resting phase subsequent to the mixing phase.

9. The process according to claim 8, wherein the room temperature of the operating theater, the internal temperature of the cartridge, the instantaneous temperature of the bond cement present in the cartridge and the state of polymerization of the bone cement present in the cartridge are automatically taken into account as process control parameters by the automatic controller.

10. The process of claim 9, wherein the temperature of the cartridge is selectively controlled by being intermittently changed in temperature during the mixing phase and during the resting phase under automatic control, whereby the bone cement at the end of the resting phase has a predetermined processing temperature which is at a temperature preferably lower than that of the operating theater concerned.

11. The process of claim 9, wherein the cartridge is introduced into the holding apparatus of the receiver before starting the mixing phase, the cartridge only being released at the end of the resting phase, preferably by manual removal from the holding apparatus.

12. The process according to claim 9, wherein the cartridge is closed by a cover which has at least one opening closed by a septum, and at least one component of the bone cement is charged into the cartridge by means of a cannula penetrating through the septum.

13. The process according to claim 12, wherein at least one component of the bone cement to be produced is stored in a storage vessel which is closed in a sterile manner and wherein the components are removed in a sterile manner from the storage vessel and charged in a sterile manner into the cartridge by means of a duct provided with a respective cannula.

* * * * *